United States Patent
Koo et al.

(10) Patent No.: US 6,297,416 B1
(45) Date of Patent: Oct. 2, 2001

(54) PROCESS FOR MAKING β-CAROTENE

(75) Inventors: Sangho Koo, #7-702, Sun-Kyung Apt., 506 Daechi-dong, Kangnam-ku, Seoul, 135-280 (KR); Hojin Choi, Yongin-shi (KR); Minsoo Park, Seoul (KR); Minkoo Ji, Seoul (KR)

(73) Assignee: Sangho Koo (KR)

( * ) Notice: Subject to any disclaimer, the term of this patent is extended or adjusted under 35 U.S.C. 154(b) by 0 days.

(21) Appl. No.: 09/435,336

(22) Filed: Nov. 5, 1999

(30) Foreign Application Priority Data

Nov. 6, 1998 (KR) ................................. 98-47549

(51) Int. Cl.$^7$ ................................. C07C 403/00
(52) U.S. Cl. ................................. 585/351
(58) Field of Search ................................. 585/351

(56) References Cited

U.S. PATENT DOCUMENTS 5,185,468 * 2/1993 Mori et al. .......................... 568/31
5,382,732 * 1/1995 Frank et al. ........................ 585/351

FOREIGN PATENT DOCUMENTS 0 523 534 A2  1/1993  (EP).

OTHER PUBLICATIONS

Choi et al., "Diallylic Sulfides as Key Structures for Carotenoid Syntheses," *J. Org. Chem.*, 64:8051–53 (1999).

Balicki et al., "$H_2O_2$—Urea/Phthalic Anyhdride System—Convenient Reagent for the Mild and Efficient Preparation of Sulfones from Organic Sulfides," *J. Prakt. Chem.*, 335:209–10 (1993).

Paust, J., "Recent Progress in Commercial Retinoids and Carotenoids," *Pure & Appl. Chem.*, 63:45–58 (1991).

Bernhard, K and Mayer, H., "Recent Advances in the Synthesis of Achiral Carotenoids," *Pure & Appl. Chem.*, 63:35–45 (1991).

Eletti–Bianchi et al., "A Two–Step Synthesis of (E)–4–Chloro–2–methylcrotonaldehyde from Isoprene. An Unprecedented Oxidative Chlorination of a 1,3–Diene Monoepoxide by Cupric Chloride," *J. Org. Chem.*, 41:1648–50 (1976).

Paust et al., Monoacetale von 2–Methyl–2–buten–1,4–dial, *Liebigs Ann. Chem.*, 2194–2205 (1976).

Julia, M. and Arnould, D., "N° 115.—Synthèses `` l'aide de sulfones. II(*).—Attachement d'un motif isoprénique éthylénique fonctionnalis´``l'extrémit´´avec ou sans production d'une double liaison supplémentaire," *Bul. de la Societ´´ Chimique de France*, 2:743–750 (1973).

Oroshnick, W. and Mallory, R., "The Reaction of Isoprene with t–Butyl Hypochlorite in Hydroxylic Solvents," *J. Am. Chem. Soc.*, 72:4608–4613 (1950).

* cited by examiner

*Primary Examiner*—Sreeni Padmanabhan
(74) *Attorney, Agent, or Firm*—Heslin & Rothenberg, P.C.

(57) ABSTRACT

A process for preparing β-carotene, represented by Formula 3

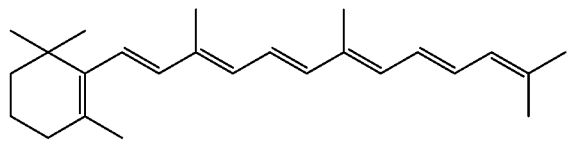

staring from a sulfone compound of Formula B

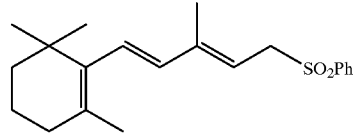

4 Claims, No Drawings

PROCESS FOR MAKING β-CAROTENE

FIELD OF THE INVENTION

The present invention relates to compounds having a polyene chain structure, and processes for preparing the same. More specifically, it relates to intermediate compounds, which can be effectively used in the synthesis of β-carotene, processes for preparing the same, processes for preparing β-carotene by using the intermediate compounds, and "retinyl sulfide," named by the present inventors, and a process for preparing the same.

BACKGROUND OF THE INVENTION

Carotenoid compounds have a polyene chain structure, and specific examples of such include β-carotene, lycopene, astaxanthin and the like. β-carotene is known as pro-vitamin A, which decomposes to vitamin A according to the needs of a living body.

Carotenoid compounds are generally used as natural pigments for foodstuffs, and are apt to selectively react with carcinogens such as singlet oxygen radical and the like, and as such, they are expected to have use as a prophylactic agent for cancers. In light of this expectation, there is an increasing need to develope a process that can effectively and efficiently synthesize the polyene chain structure.

β-carotene has been manufactured by Hoffmann-La Roche since 1954, and by BASF since 1972 [Paust, J., Pure Appl. Chem., 63:45–58 (1991)].

According to the Roche process, two $C_{19}$ molecular units are connected by using bis(magnesium halide)acetylide, and the resulting product is subjected to partial hydrogenation of the triple bond and dehydration in the presence of acid catalyst, to provide β-carotene, as shown in Scheme 1 below:

As can be seen from Scheme 1, however, the synthesis of the $C_{19}$ compound from the $C_{14}$ compound is not a convergent process, and requires two consecutive enol ether condensations, thereby providing the process with a low effectiveness.

With regard to the BASF process, β-carotene is synthesized via a Wittig reaction of $C_{15}$ phosphonium salt and $C_{10}$ dialdehyde, as is shown in Scheme 2 below. According to this process, a double bond can be effectively formed by the Wittig reaction, but the process has a further problem in that phosphine oxide ($Ph_3P=O$), produced as a by-product, cannot be easily separated or removed.

Scheme 2

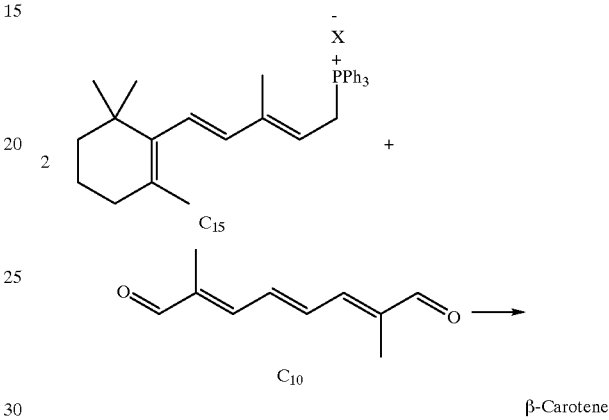

SUMMARY OF THE INVENTION

The present invention provides intermediate compounds useful for the efficient synthesis of the polyene chain Scheme 1

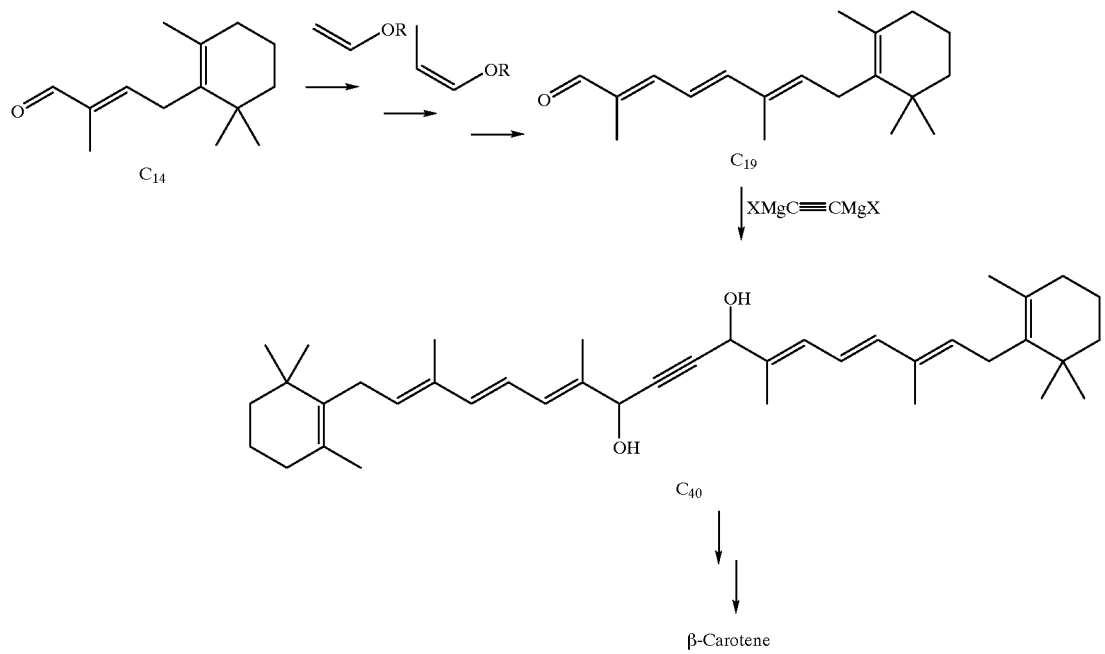

structure, taking full advantage of its symmetry and which solve the problem of by-products such as phosphine oxide by the employment of the Julia-type sulfone olefination strategy; processes for preparing the same; and processes for preparing β-carotene using the same.

The present invention also provides a novel compound having a polyene chain structure which is synthesized via the aforementioned intermediate compound, and a process for preparing the same.

The present invention further provides an improved process for preparing 2,7-dimethyl-2,4,6-octatriene-1,8-dial, a compound used in the BASF process for preparing β-carotene, which requires fewer synthetic steps than the conventional process.

Accordingly, one embodiment of the invention is a diallylic sulfide, represented by Chemical Formula 1:

Chemical Formula 1

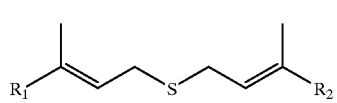

wherein, $R_1$ and $R_2$ are independently chosen from the group consisting of —CHO, —$CH_2Cl$, —$CH_2Br$, —$CH_2I$, —$CH_2OH$, —$CH_2OSO_2CF_3$, —$CH_2OSO_2Ph$, —$CH_2OSO_2C_6H_4CH_3$ and —$CH_2OSO_2CH_3$. Preferably, $R_1$ and $R_2$ are both —CHO or —$CH_2Cl$.

Another embodiment of the present invention is a process for preparing a diallylic sulfide represented by Chemical Formula 1, which comprises the steps of:

(a) oxidizing isoprene to give isoprene monoxide;

(b) reacting the isoprene monoxide with cupric halide ($CuX_2$)/lithium halide (LiX) to provide an allylic halide (A); and (c) reacting the allylic halide (A) with sodium sulfide ($Na_2S$) to produce a compound represented by Chemical Formula 1.

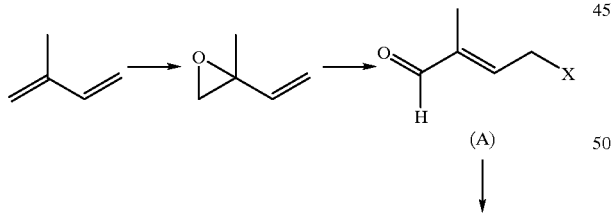

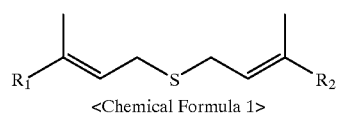

<Chemical Formula 1> wherein $R_1$ and $R_2$ are independently chosen from the group consisting of —CHO, —$CH_2Cl$, —$CH_2Br$, —$CH_2I$, —$CH_2OH$, —$CH_2OSO_2CF_3$, —$CH_2OSO_2Ph$, —$CH_2OSO_2C_6H_4CH_3$ and —$CH_2OSO_2CH_3$, and X is chosen from Cl, Br and I.

For the diallylic sulfides represented by Chemical Formula 1, wherein $R_1$ and $R_2$ are —$CH_2Cl$, —$CH_2Br$ or —$CH_2I$, the synthesis comprises the further step of reducing and halogenating the resultant product from step (c).

Step (c) is preferably performed via the sequence of: (1) adding a catalytic amount of acid to the allylic halide (A) in alcoholic solvent to form an acetal in situ; (2) reacting said acetal with sodium sulfide for a predetermined period; and (3) evaporating the solvent and hydrolyzing the residue.

Another embodiment of the present invention provides a process for preparing 2,7-dimethyl-2,4,6-octatriene-1,8-dial represented by Chemical Formula 2, which comprises the steps of:

(a) protecting the aldehyde group of allylic halide (A) to provide the corresponding acetal compound (G);

(b) reacting the acetal compound (G) with $Na_2S$ to provide di(3-formyl-3-methyl-2-propenyl)sulfide, dialkyl diacetal (H);

(c) selectively oxidizing the di(3-formyl-3-methyl-2-propenyl)sulfide, dialkyl diacetal (H) to provide the corresponding allylic sulfone compound (I);

(d) applying a Ramberg-Bäcklund reaction to the allylic sulfone compound (I) to provide the corresponding triene compound (J); and (e) hydrolyzing the triene compound (J) to provide 2,7-dimethyl-2,4,6-octatriene-1,8-dial, represented by Chemical Formula 2.

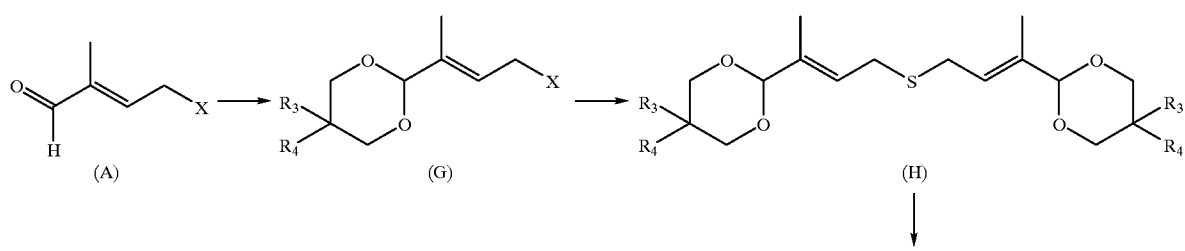

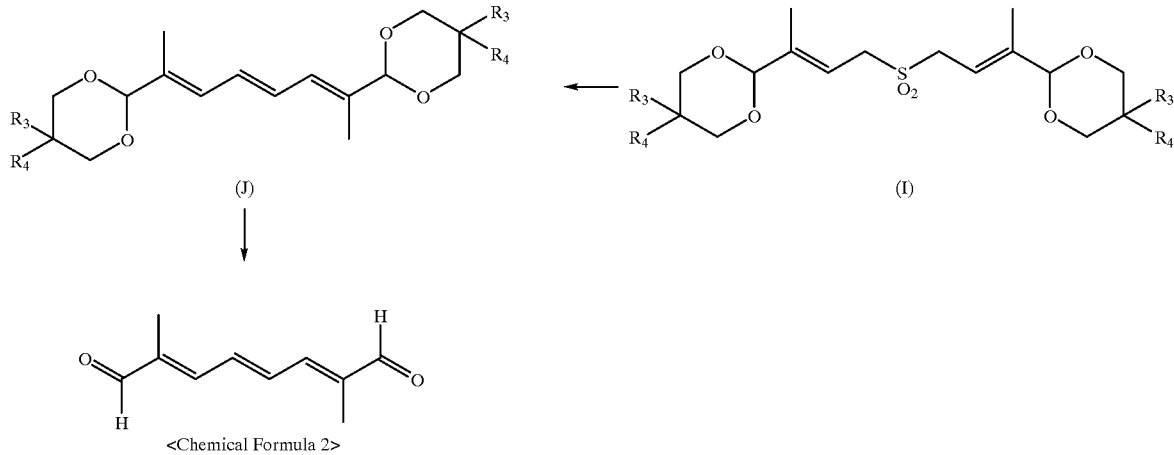

(J) → <Chemical Formula 2>

(I)

Here, X represents a halogen atom and $R_3$ and $R_4$ independently represent hydrogen or a methyl group.

In this embodiment, the selective oxidation reaction of step (c) is preferably performed by adding a mixture of urea-hydrogen peroxide (here-in-after, referred to as "UHP") and phthalic anhydride dropwise to a solution containing di(3-formyl-3-methyl-2-propenyl)sulfide, dialkyl diacetal at low temperature.

Yet another embodiment of the invention provides a process for preparing β-carotene represented by Chemical Formula 3, which comprises the steps of:

(a) deprotonating the sulfone compound (B), and reacting not more than ½ equivalent (based on the sulfone compound) of allylic sulfide (C) represented by Chemical Formula 1 ($R_1$, $R_2$=$CH_2X$, X=halogen atom) thereto, to provide sulfide compound (D);

(b) selectively oxidizing the sulfide compound (D) to prepare the sulfone compound (E);

(c) subjecting the sulfone compound (E) to a Ramberg-Bäcklund reaction to prepare 11,20-di(benzenesulfonyl)-11,12,19,20-tetrahydro-β-carotene (F); and (d) reacting 11,20-di(benzenesulfonyl)-11,12,19,20-tetrahydro-β-carotene (F) with a base to provide -β-carotene, represented by Chemical Formula 3.

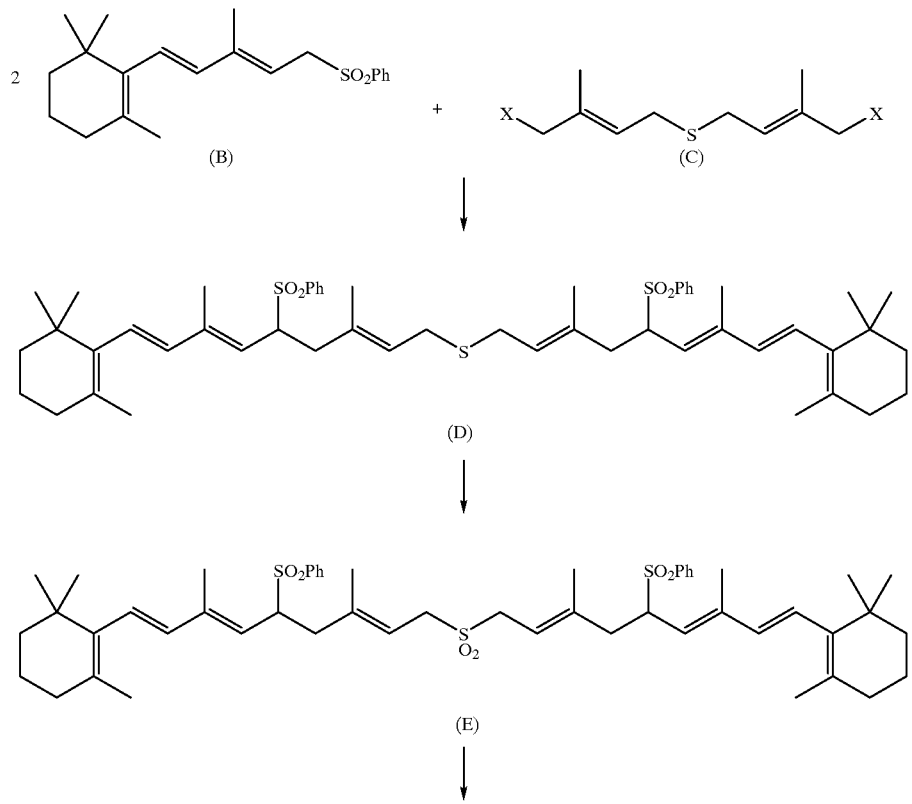

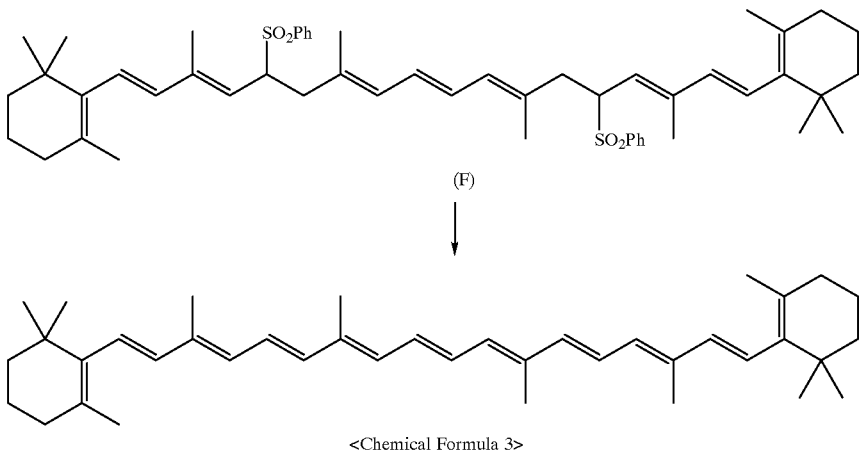

(F)

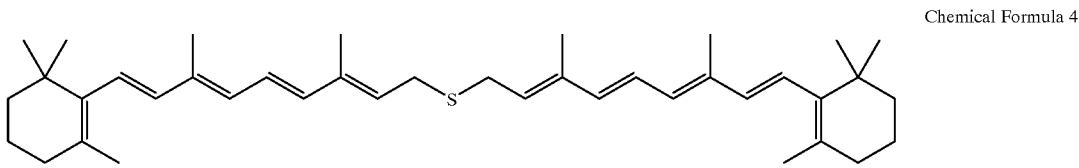

<Chemical Formula 3>

In this embodiment, when X is Cl, step (a) is preferably performed by adding a stoichiometric amount of sodium iodide (NaI) in terms of reactivity. The selective oxidation of step (b) is preferably carried out by adding a mixture of UHP and phthalic anhydride dropwise to a solution containing the sulfide compound (D) at low temperature.

The base used in step (d) is not specifically restricted. Appropriate bases include, but are not limited to, for example, $NaNH_2/NH_3$, metal alkoxides such as $CH_3OK/CH_3OH$, $CH_3CH_2OK/CH_3CH_2OH$ and $CH_3CH_2ONa/CH_3CH_2OH$, and t-BuOK/t-BuOH. Among these example, metal alkoxides are more preferable.

Yet another embodiment of the present invention provides a novel compound, retinyl sulfide, represented by Chemical Formula 4:

Chemical Formula 4

Still another embodiment of the present invention provides a process for preparing retinyl sulfide represented by the Chemical Formula 4, which comprises a Wittig reaction of diallylic sulfide (C-1) represented by Chemical Formula 1 ($R_1$ and $R_2$ are each —CHO) and the Wittig salt (K).

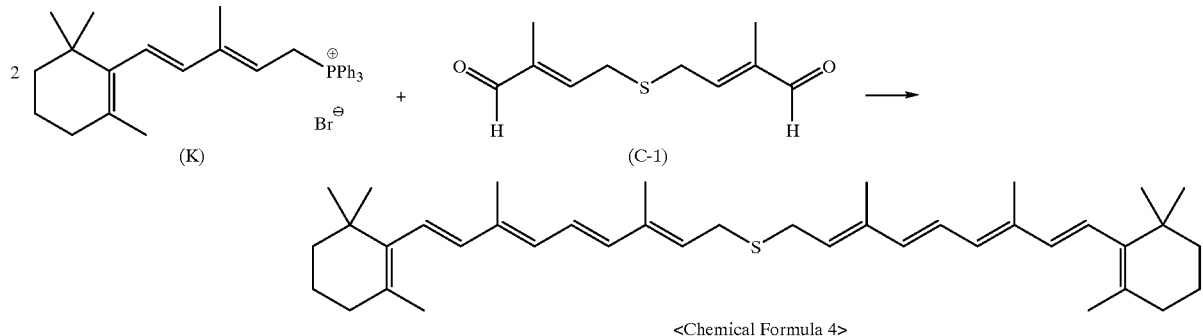

<Chemical Formula 4>

DETAILED DESCRIPTION OF PREFERRED EMBODIMENTS

The diallylic sulfide represented by Chemical Formula 1, which is used as a basic material in the synthesis of compounds having polyene chain structure, may be synthe sized according to the following procedure, illustrated in Scheme 3, below.

First, isoprene is oxidized to obtain isoprene monoxide. The oxidation may be carried out under the condition of using an oxidant such as m-chloroperoxybenzoic acid (MCPBA), or the condition of forming a corresponding halohydrin, which is then reacted with a base [*J.Am.Chem.Soc*, 72:4608 (1950)], or the like. Among these, the latter process is more preferable, when considering the regio-selectivity on two double bonds of isoprene.

Then, said isoprene monoxide is subjected to ring opening reaction by reacting with cupric halide ($CuX_2.2H_2O$)/lithium halide (LiX), to obtain allylic halide (A). For the ring opening reaction, the reaction condition disclosed in literature [*J.Org.Chem.*, 41:1648 (1976)] is referred, and the reaction condition of cupric chloride ($CuCl_2.2H_2O$)/lithium chloride (LiCl) is preferably employed.

Then, from the allylic halide (A), diallylic sulfide represented by Chemical Formula 1 is obtained.

Scheme 3

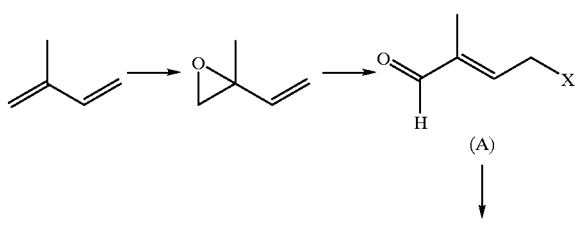

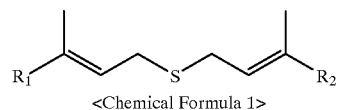

<Chemical Formula 1>

In this process, when $R_1$ and $R_2$ are each aldehyde groups, allylic halide (A) is allylated to obtain diallylic sulfide (Chemical Formula 1) which has aldehyde functional groups at both ends. The allylation is preferably carried out by adding a catalytic amount of acid such as p-toluenesulfonic acid (p-TsOH) in alcoholic solvent to form an acetal, which is then reacted with sodium sulfide and hydrolyzed. In such a reaction condition, allylation can be proceeded without side reactions. The acid such as p-TsOH serves as a catalyst that promotes the formation of acetal.

As seen in Scheme 4, below, when $R_1$ and $R_2$ are each —$CH_2X$ (wherein, X is a halogen atom), the allylic sulfide is first reduced to give the corresponding diol compound (C-1), which is then halogenated to obtain diallylic sulfide (C) in which halogen atoms have been introduced at both ends. The halogenation of diol compounds may be carried out under various reaction conditions. For example, halogenation is performed by using a reaction condition of $CH_3SO_2Cl/LiCl$, HCl, HBr, $PPh_3/CCl_4$, or the like.

Scheme 4

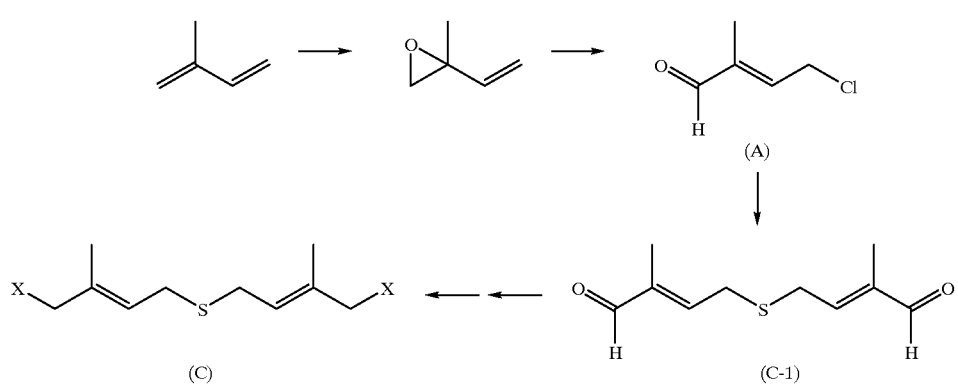

As previously discussed, 2,7-dimethyl-2,4,6-octatriene-1,8-dial represented by Chemical Formula 2 is an important compound used in the synthesis of β-carotene of Chemical Formula 3, by reacting with Wittig salt (K) according to the BASF process. Here-in-after, the process for preparing 2,7-dimethyl-2,4,6-octatriene-1,8-dial of Chemical Formula 2 is described with reference to Scheme 5 below.

First, the aldehyde group of the allylic halide (A) must be protected. The protection of aldehyde group is performed by converting the compound to the corresponding cyclic acetal compound (G) by using glycol compounds such as neopentyl glycol, propylene glycol, ethylene glycol, or the like.

The cyclic acetal compound (G) is then reacted with $Na_2S$ to obtain the corresponding allylic sulfide, dialkyl diacetal (H). The compound (H) may be used as a basic material for the synthesis of compounds having polyene chain structure.

The sulfur of the compound (H) is then selectively oxidized to obtain the corresponding allylic sulfone compound (I). The selective oxidation is performed under a condition of slowly adding an oxidant to the allylic sulfide compound (H) at low temperature. As the oxidant, peroxyphthalic acid, which is the resulting product of reaction of UHP and phthalic anhydride, is preferably used.

Through a Ramberg-Bäcklund reaction, the corresponding triene compound (J) is obtained from the allylic sulfone compound (I). Deprotection by hydrolysis of acetal groups of the triene compound (J) gives 2,7-dimethyl-2,4,6-octatriene-1,8-dial represented by Chemical Formula 2.

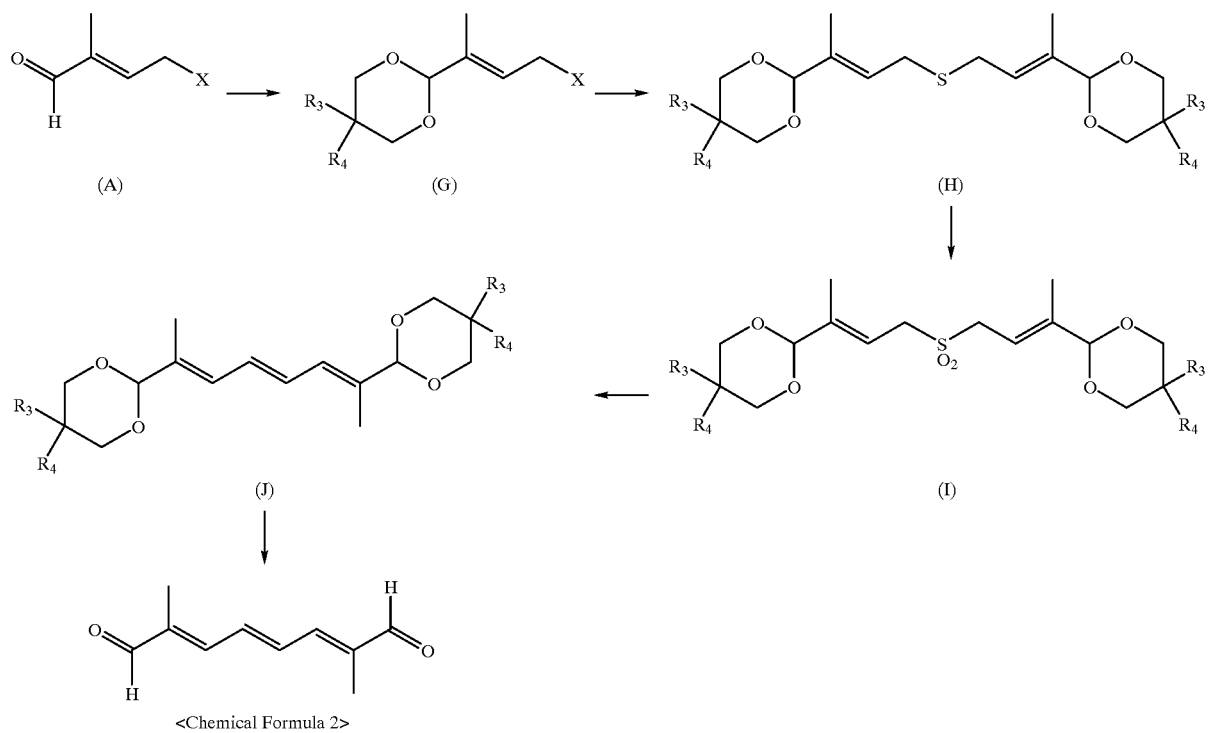

<Chemical Formula 2>

The process for preparing 2,7-dimethyl-2,4,6-octatriene-1,8-dial described herein requires fewer steps than the conventional process, making the process simpler in terms of manufacturing.

Referring now to Scheme 6, the process for preparing β-carotene of Chemical Formula 3, according to the present invention, is described. The process is characterized in that a Ramberg-Bäcklund reaction is performed on diallylic sulfone which was obtained by the oxidation of diallylic sulfide, as previously described herein.

According to the process, allylic sulfide (C) and 2 equivalents or more of sulfone compound (B) based on the amount of the allylic sulfide are first coupled according to the Julia process (*Bull.Soc.Chim.Fr.*, 1973). As a result of the coupling, the allylic sulfide (D) is obtained, which contains all the carbons required for the synthesis of β-carotene. The coupling reaction of allylic sulfide (C) with sulfone compound (B) may be carried out under various reaction conditions. If X is Cl, it is preferable to quantitatively add sodium iodide (NaI). Under such a reaction condition, the halogen atoms at both end of allylic sulfide (C) are substituted by iodine, and then allylation of the sulfone compound actively occurs.

Then, the sulfur atom only of allylic sulfide (D) is selectively oxidized to obtain the corresponding sulfone compound (E). The selective oxidation is preferably carried out under the reaction condition of adding an oxidant to the allylic sulfide compound at low temperature. Under such a reaction condition, the double bond of allylic sulfide (D) is not oxidized, but only the sulfur is selectively oxidized.

Subsequently, $SO_2$ of the central part of the structure of sulfone compound (E) is removed by forming a double bond, to give compound (F). Preferably, the reaction is carried out by applying a Ramberg-Bäcklund reaction to sulfone compound (E).

Compound (F) is then heated in the presence of alcoholic solvent and alkoxide base such as sodium alkoxide to remove two benzenesulfonyl groups, thereby obtaining β-carotene of Chemical Formula 3.

Scheme 6
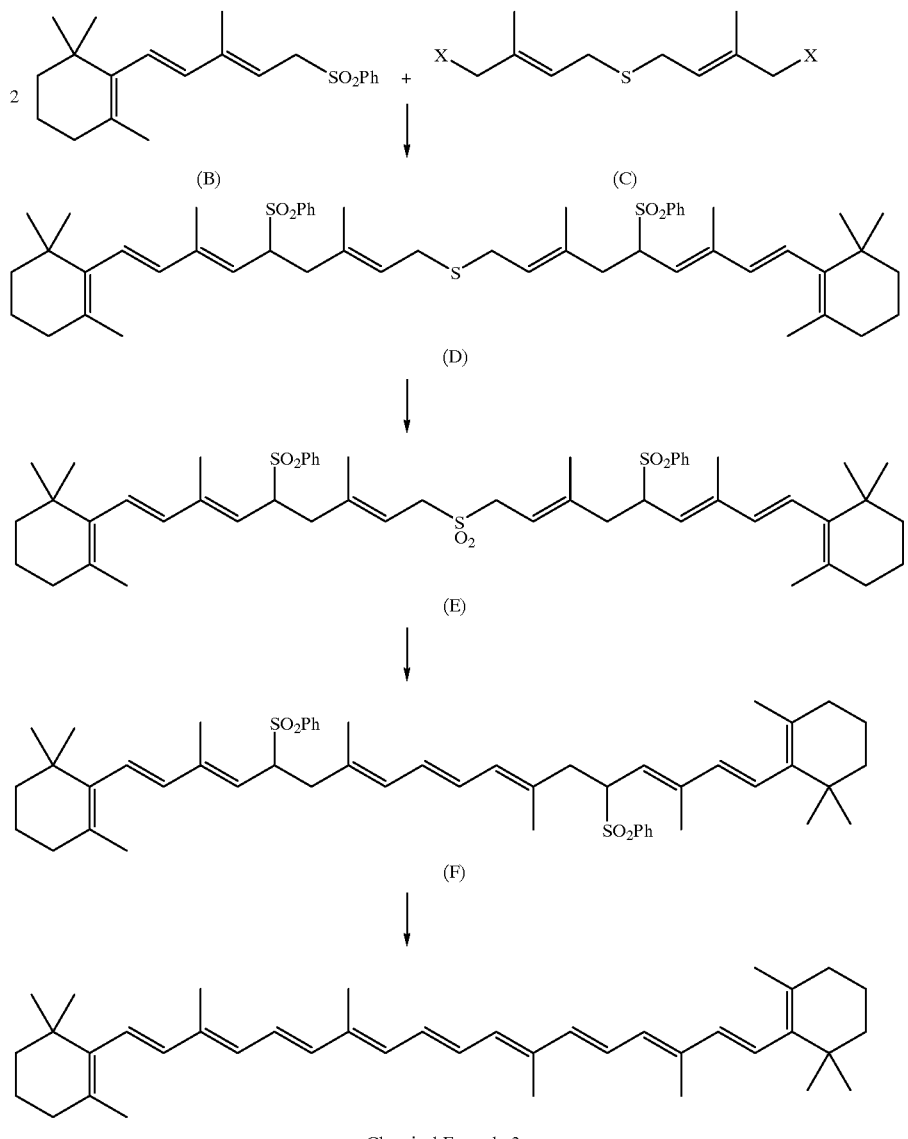
<Chemical Formula 3>
In accordance with the present invention, retinyl sulfide of Chemical Formula 4 may be obtained by a Wittig reaction wherein the allylic sulfide having aldehyde groups at both ends is reacted with Wittig salt (K), as illustrated in Scheme 7 below.
Scheme 7
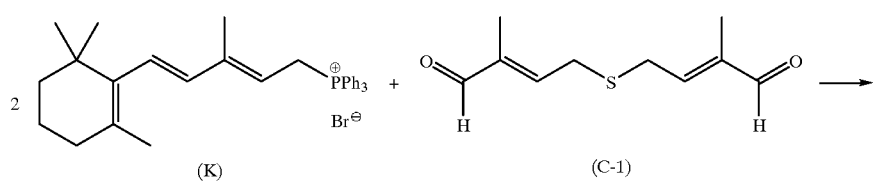

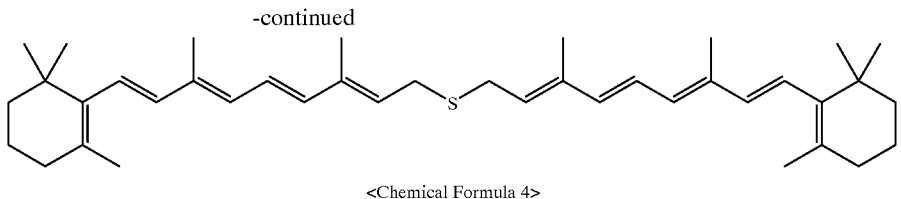

<Chemical Formula 4>

As retinyl sulfide of Chemical Formula 4 has a structure wherein the units of vitamin A are linked by a sulfur atom, the compound is expected to exhibit the activity of vitamin A.

EXAMPLES

The principles of the present invention are herein described in detail with reference to the following Examples. It should be noted, however, that these examples are provided by way of illustration only, and are not intended to limit or restrict the scope of this invention in any way.

Synthetic Example 1

Di(3-formyl-3-methyl-2-propenyl)Sulfide

To a solution of 4-chloro-2-methyl-2-buten-1-al (10.48 g, 88.2 mmol) in MeOH (80 mL) was added p-TsOH (48 mg, 0.25 mmol). The mixture was stirred for 1 h, and then $Na_2S \cdot 9H_2O$ (10.59 g, 44.1 mmol) was added. The resulting mixture was then stirred at room temperature for 10 h.

When the reaction was completed, most of solvent was removed by evaporating the reaction mixture under reduced pressure. After adding 1 M HCl (50 mL) thereto, the resultant mixture was stirred for 1 h, and extracted with methylene chloride (50 mL×3). The combined methylene chloride layer was dried over anhydrous $Na_2SO_4$, filtered, and concentrated under reduced pressure. The crude product was purified by flash chromatography over silica gel to give di-(3-formyl-3-methyl-2-propenyl)sulfide (7.43 g, 37.5 mmol) in 85% yield.

$^1$H NMR δ1.78 (6H, s), 3.44 (4H, d, J=7.7 Hz), 6.53 (2H, t, J=7.7 Hz), 9.49 (2H, s)

$^{13}$C NMR δ9.3, 29.1, 140.9, 147.5, 194.4

Synthetic Example 2

Di(4-chloro-3-methyl-2-butenyl)Sulfide

To a stirred solution of di(3-formyl-3-methyl-2-propenyl) sulfide (10.5 g, 53.0 mmol) in THF (80 mL) was added $LiAlH_4$ (1.33 g, 35.0 mmol). The mixture was stirred for 1 h, and then quenched with 1 M HCl (30 mL). The mixture was extracted with EtOAc (50 mL×3). The combined organic layer was dried over anhydrous $Na_2SO_4$, filtered, and concentrated under reduced pressure.

The above residue was dissolved in $CH_3CN$ (50 mL), and then $PPh_3$ (30.43 g, 0.116 mol) and $CCl_4$ (20 mL) were added thereto. The resulting mixture was stirred for about 5 h, diluted with ether (100 ml), and subsequently washed with 1 M HCl (20 mL×2) and $H_2O$ (30 mL).

The organic phase was dried over anhydrous $Na_2SO_4$, filtered and concentrated under reduced pressure. The crude product was purified by flash chromatography over silica gel to produce di(4-chloro-3-methyl-2-butenyl)sulfide (9.26 g, 38.7 mmol) in 73% yield.

$^1$H NMR δ1.78 (6H, s), 3.14 (4H, d, J=7.7 Hz), 4.03 (4H, s), 5.62 (2H, t, J=7.7 Hz)

MS (EI, 70eV): 240 [(M+2)$^+$], 239 [(M+1)$^+$], 238 (M$^+$), 203, 135, 102, 67

Synthetic Example 3

Di(11-benzenesulfonyl-11,12-dihydroretinyl)Sulfide

To a stirred solution of sulfone compound (B) (14.4 g, 41.8 mmol) in THF (80 mL), was added NaH (1.20 g, 50.1 mmol). The mixture was stirred for 15 min, and then di(4-chloro-3-methyl-2-butenyl)sulfide (5.0 g, 20.9 mmol) and NaI (7.5 g, 50.1 mmol) were added consecutively. The resulting mixture was stirred at room temperature for 15 h and diluted with ether. The dilute mixture was subsequently washed with 1 M HCl (20 mL×2) and distilled water (30 mL), dried over anhydrous $Na_2SO_4$, filtered, and concentrated under reduced pressure. The crude product was purified by flash chromatography over silica gel to give di(11-benzenesulfonyl-11,12-dihydroretinyl)sulfide (D) (15.7 g, 17.8 mmol) in 85% yield.

$^1$H NMR δ0.93 (6H, s), 0.96 (6H, s), 1.21 (6H, s), 1.45–1.65 (8H, m), 1.63 (12H, s), 2.00 (4H, t, J=6.0 Hz), 2.39 (2H, dd, J=13.2, 11.5 Hz), 2.90 (4H, d, J=6.8 Hz), 2.90–3.10 (2H, m), 4.02 (2H, dt, $J_d$=3.1, $J_t$=11.0 Hz), 5.07 (2H, d, J=10.3 Hz), 5.21 (2H, t, J=7.0 Hz), 5.93 (4H, s), 7.45–7.53 (4H, m), 7.58–7.65 (2H, m, 7.8–7.84 (4H, m)

$^{13}$C NMR δ12.3, 16.0, 16.0, 19.2, 21.6, 28.9, 28.9, 33.0, 34.2, 37.4, 39.5, 64.1, 122.3, 125.8, 129.2, 129.6, 130.2, 130.4, 134.0, 134.4, 136.8, 138.1, 138.5, 143.2

Synthetic Example 4

Di(11-benzenesulfonyl-11,12-dihydroretinyl)Sulfone

The mixture of UHP (6.88 g, 73.1 mmol) and phthalic anhydride (5.41 g, 36.5 mmol) in $CH_3CN$ (70 mL) was stirred vigorously at room temperature for 2 h to give a clear solution. This solution was charged in a dropping funnel, and slowly added over three hour period to a solution of di(11-benzenesulfonyl-11,12-dihydroretinyl)sulfide (D) (10.8 g, 12.2 mmol) in $CH_3CN$ (30 mL). The temperature of the reaction mixture was adjusted to be maintained at 0° C.

When the dropping was complete, the reaction mixture was stirred at 0° C. for 1 h. After adding 1 M aqueous HCl (30 mL) thereto, the reaction mixture was extracted with ether (50 mL×2). The combined ether layer was dried over anhydrous $Na_2SO_4$, filtered, and concentrated under reduced pressure to give a white solid. The crude solid was dissolved in $CHCl_3$, and insoluble solid was filtered off The filtrate was concentrated, and the residue was purified by flash chromatography over silica gel to give di(11-benzenesulfonyl-11, 12-dihydroretinyl)sulfone (8.06 g, 8.77 mmol) in 72% yield. Two stereo isomers of the obtained allylic sulfone compound were found, and one of which was isolated in pure state through silica gel column chromatography.

$^1$H NMR δ0.91 (6H, s), 0.96 (6H, s), 1.22 (6H, s), 1.37–1.49 (4H, m), 1.55–1.67 (4H, m), 1.62 (6H, s), 1.65 (6H, s), 1.99 (4H, t, J=5.9 Hz), 2.47 (2H, dd, J=13.0, 11.3

Hz), 3.05 (2H, d, J=13.0 Hz), 3.47 (4H, d, J=4.5 Hz), 4.06 (2H, dt, $J_d$=3.1, $J_t$=10.8 Hz), 5.07 (2H, d, J=10.5 Hz), 5.24 (2H, t, J=7.4 Hz), 5.92 (2H, A of ABq, J=16.4 Hz), 5.97 (2H, B of ABq, J=16.4 Hz), 7.40–7.55 (4H, m), 7.55–7.70 (2H, m), 7.75–7.90 (4H, m)

$^{13}$C NMR δ12.3, 17.0, 19.1, 21.5, 28.7, 28.8, 32.8, 34.0, 37.3, 39.3, 51.0, 63.4, 114.1, 121.0, 128.8, 129.0, 129.3, 129.7, 133.7, 135.5, 137.1, 137.2, 140.8, 142.8

Synthetic Example 5

11,20-Dibenzenesulfonyl-11,12,19,20-tetrahydro-β-carotene

To a stirred solution of di(11-benzenesulfonyl-11,12-dihydroretinyl)sulfone (E) (1.51 g, 1.64 mmol) in t-BuOH (20 mL) and CCl$_4$ (20 mL), was added KOH (1.85 g, 32.9 mmol) under argon atmosphere. The mixture was stirred vigorously for 5 h.

When the reaction was completed, most of solvent was removed from the reaction mixture under reduced pressure. The crude product was dissolved in CH$_2$Cl$_2$ (60 mL) and washed with 1 M HCl (20 mL). The combined methylene chloride layer was dried over anhydrous Na$_2$SO$_4$, filtered, and concentrated. The crude product was purified by flash chromatography over silica gel to give 11,20-dibenzenesulfonyl-11,12,19,20-tetrahydro-β-carotene (F) (932 mg, 1.13 mmol) in 69% yield.

$^1$H NMR δ0.93 (6H, s), 0.96 (6H, s), 1.20 (6H, s), 1.37–1.50 (4H, m), 1.53–1.65 (4H, m), 1.63 (6H, s), 1.68 (6H, s), 1.98 (4H, br s), 2.45 (2H, dd, J=13.0, 11.6 Hz), 3.04 (2H, d, J=14.2 Hz), 4.05 (2H, dt, $J_d$=3.0, $J_t$=10.9 Hz), 5.82–5.98 (2H, m), 5.92 (4H, s), 6.15–6.28 (2H, m), 7.40–7.54 (4H, m), 7.56–7.67 (2H, m), 7.76–7.9 (4H, m)

$^{13}$C NMR δ12.3, 12.3, 16.7, 16.8, 19.1, 21.5, 28.8, 32.8, 34.1, 39.4, 64.2, 121.4, 127.8, 128.1, 128.7, 129.0, 129.3, 129.5, 132.9, 133.5, 136.0, 137.2, 137.6, 142.1

Synthetic Example 6

β-Carotene

Sodium (674 mg, 29.3 mmol) was added to a stirred solution of 11,20-di(benzenesulfonyl)-11,12,19,20-tetrahydro-β-carotene (F) (602 mg, 0.73 mmol) in EtOH (20 mL) under argon atmosphere. The reaction mixture was heated under reflux for 10 h with vigorous stirring.

When the reaction was completed, the reaction mixture was concentrated under reduced pressure to remove most of the solvent. Toluene (50 mL) was added thereto to dissolve the residue, and the resultant mixture was washed with 1 M HCl, dried over anhydrous Na$_2$SO$_4$, filtered, and concentrated under reduced pressure. The crude product was purified by flash chromatography over silica gel to give exclusively trans-β-carotene of Chemical Formula 3 (295 mg, 0.55 mmol) in 75% yield.

The NMR data for trans-β-carotene prepared as synthetic example 6 was identical to that of the authentic trans-β-carotene sample:

$^1$H NMR δ1.03 (12H, s), 1.44~1.49 (4H, m), 1.55~1.67 (4H, m), 1.72 (6H, s), 1.98 (12H, s), 2.03 (4H, t, J=6.3 Hz), 6.15 (2H, A of ABq, J=16.5 Hz), 6.16 (2H, d, J=11.4 Hz), 6.18 (2H, B of ABq, J=16.5 Hz), 6.26 (2H, m), 6.37 (2H, A of ABq, J=14.9 Hz), 6.64 (2H, m), 6.66 (2H, d of ABq, $J_d$=11.4, $J_{AB}$=14.9 Hz) ppm.

Synthetic Example 7

Di(3-formyl-3-methyl-2-propenyl)Sulfide, Dineopentyl Diacetal

To a solution of 4-chloro-2-methyl-2-buten-1-al (15.8 g, 0.134 mol) in toluene (100 mL) were added neopentyl glycol (16.7 g, 0.161 mol) and p-TsOH (190.2 mg, 6.7 mol). The mixture was heated under reflux for 3 h and cooled to room temperature. The mixture was diluted with ether (100 mL) and washed with distilled water (20 mL×3). The organic phase was dried over anhydrous Na$_2$SO$_4$, filtered and concentrated under reduced pressure. The crude product was purified by flash chromatography over silica gel to give acetal (G) (R$_3$, R$_4$=CH$_3$) (20.6 g, 0.100 mol) in 75% yield.

$^1$H NMR δ0.73 (3H, s), 1.20 (3H, s), 1.79 (3H, s), 3.47 (2H, A of ABq, J=11.0 Hz), 3.62 (2H, B of ABq, J=11.0 Hz), 4.09 (2H, d, J=7.9 Hz), 4.72 (1H, s), 5.85 (1H, t, J=7.2 Hz)

$^{13}$C NMR δ11.3, 21.7, 22.8, 30.1, 39.4, 77.1, 103.4, 124.2, 138.1

MS (EI, 70 eV): 205 [(M+2)$^+$], 203 (M$^+$), 169, 119, 83, 69, 55.

The above acetal (G) (20.6 g, 0.100 mmol) was dissolved in MeOH (100 mL) and Na$_2$S.9H$_2$O (12.0 g, 50 mmol) was added thereto. The resulting mixture was stirred at room temperature for 10 h.

When the reaction was completed, most of solvent was removed by evaporating under reduced pressure. The crude oil was dissolved in ether (100 mL) and washed with distilled water (30 mL×2), dried over anhydrous Na$_2$SO$_4$, filtered and concentrated under reduced pressure. The crude product was purified by flash chromatography over silica gel to give di(3-formyl-3-methyl-2-propenyl)sulfide, dineopentyl diacetal (17.6 g, 47.5 mmol) in 95% yield.

$^1$H NMR δ0.68 (6H, s), 1.15 (6H, s), 1.68 (6H, s), 3.09 (4H, d, J=7.5 Hz), 3.43 (4H, A of ABq, J=11.1 Hz), 3.58 (4H, B of ABq, J=11.1 Hz), 4.66(2H, s), 5.63 (2H, t, J=7.5 Hz)

$^{13}$C NMR δ11.2, 21.8, 22.9, 28.0, 30.1, 77.1, 104.4, 125.4, 135.8

Synthetic Example 8

2,7-Dimethyl-2,4,6-octatriene-1,8-dial of Chemical Formula 2

The mixture of UHP (5.17 g, 54.9 mmol) and phthalic anhydride (4.07 g, 27.5 mmol) in CH$_3$CN (30 mL) was stirred vigorously at room temperature for 2 h to give a clear solution. This solution was charged in a dropping funnel, and slowly added over three hour period to a solution of di(3-formyl-3-methyl-2-propenyl)sulfide dineopentyl diacetal (3.39 g, 9.15 mmol) in CH$_3$CN (20 mL). The temperature of the reaction mixture was adjusted to be maintained at 0° C.

When the dropping was completed, the reaction mixture was stirred at 0° C. for 1 h. After adding 30 mL of distilled water thereto, the reaction mixture was extracted with ether (100 mL). The combined ether layer was dried over anhydrous Na$_2$SO$_4$, filtered, and concentrated under reduced pressure to give a white solid. The crude solid was dissolved in CHCl$_3$, and insoluble solid was filtered off. The filtrate was concentrated under reduced pressure, and the residue was purified by flash chromatography over silica gel to give allylic sulfone compound (I) (R$_3$, R$_4$=CH$_3$) (2.94 g, 7.3 mmol) in 80% yield.

$^1$H NMR δ0.75 (6H, s), 1.20 (6H, s), 1.79 (6H, s), 3.50 (4H, A of ABq, J=10.9 Hz), 3.66 (4H, B of ABq, J=10.9 Hz), 3.72 (4H, d, J=7.7 Hz), 4.76 (s, 2H), 5.79 (2H, t, J=7.7 Hz).

The allylic sulfone compound (I) (R$_3$, R$_4$=CH$_3$) (3.00 g, 7.45 mmol) was dissolved in a mixed solvent of t-butanol (30 mL) and carbon tetrachloride (30 mL), and KOH (4.18 g, 74.5 mmol) was added thereto under argon atmosphere. The reaction mixture was stirred vigorously for 6 h.

When the reaction was completed, most of solvent was removed from the reaction mixture under reduced pressure. The crude product was dissolved in ether (70 mL), and washed with distilled water (20 mL×2). The organic layer was filtered and concentrated. The crude product was purified by flash chromatography over silica gel to give triene compound (J) ($R_3$, $R_4$=$CH_3$) (2.04 g, 6.07 mmol) in 82% yield.

$^1$H NMR δ0.73 (6H, s), 1.22 (6H, s), 1.85 (6H, s), 3.51 (4H, A of ABq, J=9.8 Hz), 3.66 (4H, B of ABq, J=9.8 Hz), 4.75 (2H, s), 6.30 (2H, d, J=8.1 Hz), 6.50 (2H, dd, J=7.7, 2.8 Hz)

$^{13}$C NMR δ11.7, 21.4, 22.6, 29.8, 76.8, 103.9, 127.6, 129.1, 134.2

The triene compound (J) ($R_3$, $R_4$=$CH_3$) (66 mg, 1.97 mmol) was dissolved in THF (30 mL), and 1 M HCl (30 mL) was added thereto. The reaction mixture was stirred at room temperature for 3 h. Then the reaction mixture was extracted with ether (50 mL×2). The organic layer was filtered and concentrated. The crude product was purified by flash chromatography over silica gel to give 2,7-dimethyl-2,4,6-octatriene-1,8-dial (226 mg, 1.38 mmol) in 70% yield.

$^1$H NMR δ1.96 (6H, s), 7.00–7.15 (4H, m), 9.56 (2H, s)
$^{13}$C NMR δ9.7, 134.3, 140.8, 146.1, 194.4

Synthetic Example 9

Retinyl Sulfide of Chemical Formula 4

Wittig salt compound (K) (7.75 g, 14.2 mmol) and di(3-formyl-3-methyl-2-propenyl)sulfide (1.41 g, 7.1 mmol) of Chemical Formula 1 were dissolved in DMF (50 mL). The reaction mixture was sufficiently stirred at −20° C.

To the reaction mixture, sodium methoxide (8.1 g, 0.15 mmol) was added, and the resultant mixture was stirred for 30 minutes. After raising the temperature to room temperature, the reaction mixture was farther stirred for 3 h.

The reaction mixture was diluted with toluene (100 ml), and washed with 1M HCl (30 mL×2). The organic layer was dried over anhydrous $Na_2SO_4$, filtered, and concentrated. The crude product was purified by flash chromatography over silica gel to give retinyl sulfide (2.75 g, 4.82 mmol) comprising three stereo isomers in 68% yield.

$^1$H NMR for the major isomer δ0.97 (6H, s), 1.38~1.47 (2H, m), 1.54 (3H, s), 1.55~1.65 (2H, m), 1.59 (3H, s), 1.77 (3H, s), 1.92 (2H, t, J=6.3 Hz), 2.88 (2H, d, J=6.4 Hz), 4.96 (1H, m), 5.24 (3H, m), 5.54 (1H, t, J=6.8 Hz), 6.05 (1H, d, J=15.6 Hz). Characteristic peaks for the minor isomers: δ1.55 (3H, s), 1.58 (3H, s), 2.69 (2H, d, J=7.1 Hz), 2.69 (2H, d, J=6.8 Hz), 5.49 (1H, t, J=6.4 Hz), 6.01 (1H, d, J=7.5 Hz).

As described above, when β-carotene is prepared according to Synthetic Examples 1 to 6, the process becomes simpler as compared to the conventional processes, and the problem involved with the by-products such as phosphine oxide can be avoided. According to Synthetic Example 8, 2,7-dimethyl-2,4,6-octatriene-1,8-dial of Chemical Formula 2 can be prepared through synthetic steps having two stages reduced as compared with the conventional process.

In addition, the yield of retinyl sulfide of Chemical Formula 4 prepared according to Synthetic Example 9 was 68%. Retinyl sulfide is expected to have an activity of vitamin A.

INDUSTRIAL APPLICABILITY

The allylic sulfide compounds of Chemical Formula 1 according to the present invention may be effectively used as intermediates for the synthesis of compounds having polyene chain structure such as β-carotene. The compound represented by Chemical Formula 2, 2,7-dimethyl-2,4,6-octatriene-1,8-dial, is also an important intermediate used for the synthesis of β-carotene. According to the present invention, the process for 2,7-dimethyl-2,4,6-octatriene-1,8-dial can be shortened by two stages as compared to the process according to BASF, so that the time required for the production and production cost may be reduced.

According to the present invention, allylic sulfide compound (D) is oxidized to provide the corresponding diallylic sulfone compound, to which a Ramberg-Bäcklund reaction is applied to provide the carotene compound of Chemical Formula 3, having the polyene chain structure. When β-carotene is prepared according to the principles of the present invention, the process can be easily performed as compared to the conventional process according to BASF or Roche, and problems involved with by-products are avoided.

Retinyl sulfide of Chemical Formula 4 is expected to have the activity of vitamin A.

We claim:
1. A process for preparing β-carotene, represented by Formula 3

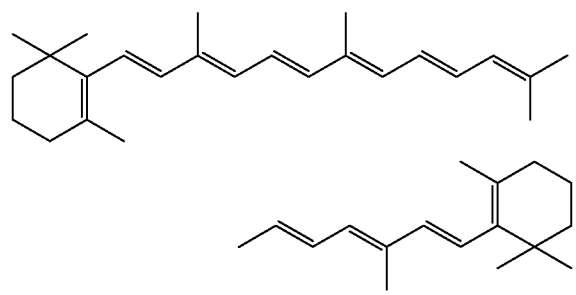

which comprises the steps of
a) providing a sulfone compound of Formula B

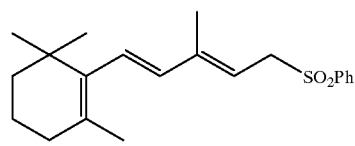

(b) deprotonating the sulfone compound of Formula B and reacting not more than ½ equivalent, based upon the sulfone compound, of an allylic sulfide, represented by Formula C

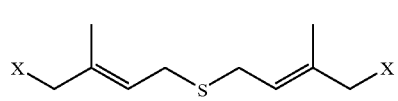

wherein X is a halogen, to provide a sulfide compound of Formula D

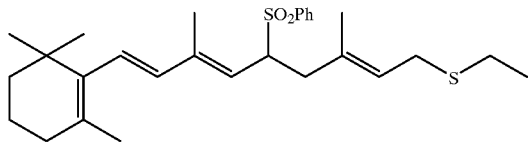

D

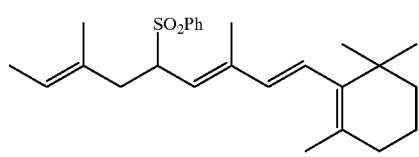

(c) oxidizing the sulfide compound of step (b) to provide a sulfone compound of

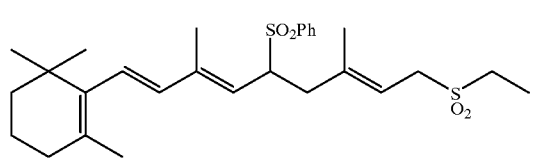

E

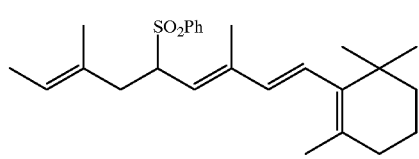

(d) subjecting the sulfone compound of step (c) to a Ramberg-Bäcklund reaction to provide 11,20-di(benzenesulfonyl)-11,12,19,20 tetrahydro-β-carotene of Formula F

F

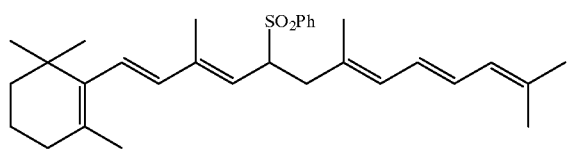

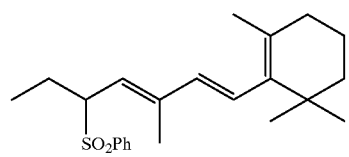

(e) reacting the product of step (d) with a base to obtain β-carotene of Formula 3.

2. The process according to claim 1, wherein X is Cl and step (b) further comprises adding a stoichiometric amount of sodium iodide to the reaction mixture.

3. The process according to claim 1, step (c) comprises adding a mixture of urea-hydrogen peroxide and phthalic anhydride to the sulfide compound of step (b).

4. The process according to claim 1, wherein step (e) comprises reacting the product of step (d) with a metal alkoxide.

* * * * *